United States Patent
Baldwin et al.

(10) Patent No.: US 8,562,575 B2
(45) Date of Patent: Oct. 22, 2013

(54) HOLISTIC BREAST PATCH

(75) Inventors: Samuel Earl Baldwin, Los Angeles, CA (US); Mary L. Benson, Los Angeles, CA (US)

(73) Assignees: Samuel E. Baldwin, Los Angeles, CA (US); Mary L. Benson, Los Angeles, CA (US)

( * ) Notice: Subject to any disclaimer, the term of this patent is extended or adjusted under 35 U.S.C. 154(b) by 0 days.

(21) Appl. No.: 13/342,917

(22) Filed: Jan. 3, 2012

(65) Prior Publication Data

US 2013/0172832 A1    Jul. 4, 2013

(51) Int. Cl.
*A61F 13/00*    (2006.01)

(52) U.S. Cl.
USPC .......................................... 604/304; 604/289

(58) Field of Classification Search
USPC ........ 604/304, 74, 75, 289, 305, 309; 450/36; 607/50, 112, 114; 606/33
See application file for complete search history.

(56) References Cited

U.S. PATENT DOCUMENTS

| | | | |
|---|---|---|---|
| 5,006,525 A | 4/1991 | Schaus | |
| 5,732,714 A * | 3/1998 | Morrissey et al. | 128/846 |
| 6,653,520 B1 * | 11/2003 | Mouton | 602/45 |
| 6,890,738 B2 | 5/2005 | Walker | |
| 2008/0033506 A1 * | 2/2008 | Flick | 607/50 |

* cited by examiner

*Primary Examiner* — Tatyana Zalukaeva
*Assistant Examiner* — Benedict L Hanrahan

(57) ABSTRACT

The Holistic Breast Patch is the first known, non-pharmaceutical, effective device available which inhibits prolactin production safely and aids the relief of discomfort from breast engorgement pain by drying breast milk after pregnancy. The benefits of treatment of prolactin dependent diseases remain to be fully disclosed. It works transdermally and is comprised of a unique, approximately 1½ inch by ¾ inch natural and organic carbonyl disc housed within cotton gauze and non-stick adhesive Telfa®. It meets the Federal Drug Administration's definition of a non-significant risk device (21 CFR 812). Its use will aid in the treatment of prolactin dependent diseases and conditions and eliminate the serious risks of health complications and fatalities that have been documented by the use of prescription drugs, hormones and pharmaceuticals lacking FDA approval for this use by women. Wearing the Patch device is both easy and convenient. Using it as directed expedites the suppression of lactation, significantly reducing the duration of lactation and also alleviates pain associated with breast milk engorgement, in addition to the benefits derived from use in prolactin dependent and related disease treatment.

1 Claim, 4 Drawing Sheets

HOLISTIC BREAST PATCH

BACKGROUND OF THE INVENTION (1) Field of the Invention

The present invention relates to certain new and useful improvements in aiding the comfort of breast engorgement pain and breast milk suppression and, more particularly, to an improved apparatus and method residing in the provision of a specified patch which is worn over a woman's chest to aid engorgement pain and suppression of breast milk (2) Description of the Related Art This invention endeavors to provide a safe, comfortable, easy to use device to relieve the pain and discomfort associated with postpartum breast milk engorgement, to expedite the suppression of lactation for women who choose not to breast-feed, and to aid in the treatment of prolactin dependent and related diseases and disorders. This is accomplished by inhibiting the production of prolactin which suppresses lactation.

After pregnancy, a woman naturally produces breast milk for a period of time. The length of time for postpartum milk production varies depending upon whether or not the mother breast-feeds and how long she breast-feeds. For breast-feeding mothers, milk production can continue up to twenty four months or longer. For non-breast-feeding women, the duration is impacted by whether or not and for how long her breasts were pumped or stimulated to produce milk. Women who choose not to breast-feed experience discomfort and pain due to breast engorgement. Relief is sought through breast pumping stimulation, which prolongs production and delays suppression of milk production; ice packs; breast binding, which can cause mastitis; and various other means that have proven to be dangerous or otherwise unsuccessful.

According to Treatment for Lactation Suppression, Little Progress in One Hundred Years (Am J Obstet. Gynecol. 1998; 179:1485-90) "Engorgement and breast pain may encompass most of the first postpartum week. Up to one third of women who do not breast-feed and who use a brassiere or binder, ice packs, or analgesics may experience severe breast pain. Specific studies of nonpharmacologic methods of lactation suppression were limited and inconclusive. Available data suggest that many women using currently recommended strategies for treatment of symptoms may nevertheless experience engorgement or pain for most of the first postpartum week.

There is no Federal Drug Administration (FDA) approved treatment for the relief of breast milk engorgement pain. Prescription drugs such as, Parlodel® (bromocriptine mesylate), a previously FDA approved lactation suppressant and estrogens and androgens (gonadotrophic hormones) have been prescribed and are possibly still being used as a prolactin inhibitor to suppress milk production for breast engorgement relief and to treat prolactin related disease and conditions.

Parlodel® inhibits the secretion of the hormone, prolactin, from the pituitary gland. It also mimics the action of dopamine, a chemical lacking in the brain of a person with Parkinson's disease. Parlodel®, and estrogens and androgens have been used to treat a variety of medical conditions, including lactation suppression, infertility, menstrual problems (such as galactorrhea), and prolactin dependent amenorrhea, with or without excessive production of milk. However, it has been well documented in the literature that these drugs and hormones have produced adverse effects including death. Some of the documentation is in the literature that follows.

To address problems involved in the prior art, reference is made to the Dec. 1, 1989 FDA Consumer which states "FDA has asked that the manufacturer of the drug Parlodel® (bromocriptine) to stop labeling the drug for use in drying up milk production and preventing breast engorgement in mothers who don't breast-feed. (Parlodel® is approved for treatment of Parkinson's disease.)

In a related move, FDA requested that the manufacturers of products containing estrogen and androgens stop labeling these gonadotrophic hormones as lactation suppressants. FDA's Fertility and Maternal Health Drugs Advisory Committee suggested the changes, in part, because these drugs, which can have serious side effects, benefit only 10 percent of the women who use them to suppress lactation. Also, the drugs' effectiveness is diminished because of the high occurrence of rebound. Breasts become engorged again after the woman stops taking the drugs.

The Health facts newspaper (Sep. 1, 1994, edition) states "Parlodel®, a drug widely used to suppress breast milk following childbirth has finally been withdrawn by its manufacturer, Sandoz, five years after it was found to be dangerous and ineffective." The action came on the heels of a national TV investigative report and a lawsuit against the FDA by the Public Citizen's Health Research Group and the National Women's Health Network.

The two consumer groups took legal action against the FDA because the agency failed to ban the drug as a lactation suppressant after receiving reports of its dangers. Since 1980, according to Public Citizen, the FDA had received 531 adverse reactions reports, including 32 deaths, 14 from stroke and five heart attacks. Among the nonfatal reactions, there were 36 strokes, 14 heart attacks, and 98 seizures; many of these cases involve permanent disability. Underreporting is a very real possibility as the FDA's post market surveillance system is notoriously weak (Rx News August 1994)."

In the Oct. 1, 1994, issue of Trial Magazine, it is stated "Under a barrage of consumer criticism and a lawsuit, the manufacturer of Parlodel® said it will no longer market the drug as a lactation suppressant. The drug has been blamed for the deaths of at least 32 new mothers and for medical problems in hundreds of women since it received U.S. Food and Drug Administration (FDA) approval in 1980."

In the United States, the sharp restriction in the use of pharmaceuticals to aid the suppression of breast milk and the discomfort and pain from engorgement, has resulted in essentially no recognized mechanism for lactation suppression and relieving the discomfort of breast milk engorgement. The formerly used pharmaceutical items are no longer available as a prescription for lactation suppression. They are however, offered online through Canadian and United Kingdom Pharmacies without a prescription. This availability again exposes mothers to the serious documented risks. Accordingly, there is an urgent need for an alternative method which will relieve the discomfort of breast engorgement pain and expedite the suppression of breast milk production in a safe, convenient, efficient, and legal manner.

"There is increasing evidence that prolactin (PRL), a hormone/cytokine, plays a role in breast, prostate, and colorectal cancers via local production or accumulation." (Cancer Res. 2009; 69(12):5226-33) Breast cancer is the most common cancer among American women, except for skin cancers. The chance of developing invasive breast cancer at some time in a woman's life is a little less than 1 in 8 (12%). Breast cancer is the second leading cause of cancer death in women, exceeded only by lung cancer." (American Cancer Society, Dec. 9, 2011) "Other than skin cancer, prostate cancer is the most common cancer in American men. About 1 man in 6 will be diagnosed with prostate cancer during his lifetime. Prostate cancer is the second leading cause of cancer death in American men, behind only lung cancer." (American Cancer Society Oct. 12, 2011)

Current treatment of prolactin dependent and related diseases and conditions involves the use of neutralizing prolactin receptor antibodies and antigen binding fragments, through pharmaceutical agents including dopamine antagonists and monoclonal drugs. These pharmaceutical drugs affect the amino acid sequence of the extracellular domain of the prolactin receptor and the nucleic acid sequence whereby the pharmaceutical composition antagonizes the prolactin receptor mediated signaling. (US Fed. News Service, Including US State News, Jun. 16, 2011, WIPO Assigns patent To Bayer Schering Pharma. for "Neutralizing Prolactin Receptor Antibodies and their therapeutic use." abstract). Recent studies indicate "Several PRL receptor (PRLR) antagonists have been identified in the past decades, but their in vivo growth inhibitory potency was restricted by low receptor affinity, rendering them pharmacologically unattractive for clinical treatment." PEDS Oxford Journals; Life Sciences & Medicine; Volume 24, Issue 11

SUMMARY OF THE INVENTION

Postpartum milk suppression will readily occur without intervention. This process, however can be lengthy, tedious, and is usually painful without the aid of breast pumps and medication to relieve breast engorgement pain.

This very surprising discovery, that a "Holistic (Carbonyl Group) Breast Patch", referred to as a "Patch", when worn by postpartum women in a prescribed regimen will significantly reduce the time for lactation suppression to occur. When lactation is suppressed, the discomfort and pain associated with breast milk engorgement is relieved and the support of prolactin dependent and related diseases and disorders is interrupted by inhibitory prolactin production.

The approximately 1 inch by ¾ inch breast patch is worn by postpartum women, generally in the form of a Telfa® pad which the mother applies to her chest. The FDA approved Telfa® pad consisting of inactive ingredients is the exterior housing for the "Carbonyl Group" disc containing the active ingredients.

It is easily applied by the mother between her breasts. This unique patch can be put on and removed easily without pain due to Telfa's® nonstick adhesive properties. In the rare event of adhesive sensitivity, the Patch can be applied with latex free microspore cotton tape.

The scientific method of the "Holistic Breast Patch" is called "transdermal" because the patch is applied to the skin for the "Carbonyl Group" elements of the Patch to cause lactation suppression in a much shorter length of time than without the aid of the Patch.

The Patch is highly effective in that it successfully suppresses postpartum milk production in three to eight days by comparison to six to eight weeks or longer without its use.

The Patch conveniently allows postpartum mothers, who choose not to breast-feed, the opportunity to recover from childbirth, return to employment more quickly, protect the newborn from HIV transmission from an HIV positive mother or ease the grief for the mother who suffers the loss of her newborn.

Furthermore, the Holistic Breast Patch is safe in that it has no known side effects. Therefore, no warnings or precautions are required. When marketed, it will eliminate all of the dangerous, reported fatal adverse effects of previously used methods to quickly produce lactation suppression for relief of pain associated with breast milk engorgement. It will also provide a safe and effective method for treatment of diseases and conditions that require the inhibition of prolactin production. The interior disc of this product consists of all natural fibers and it is labeled by the Food & Drug Administration (FDA) as a device and not a drug. The FDA has determined that the Patch meets its definition for a non-significant risk device (21 CFR 812).

Many other advantages and other purposes will be made more fully apparent from a consideration of the forms in which this invention may be embodied. These forms are illustrated in the following detailed description of the invention and in the accompanying drawings. However, this detailed description and the drawings are set forth only for the purpose of illustrating the general principles of this invention and are not limited to this illustration only.

The primary objective of this invention is to provide a safe device to significantly reduce the time to achieve lactation suppression, thus expediting the relief of discomfort of breast engorgement pain in the form of a breast patch which is applied between a woman's breasts.

It is a further object of the present invention to provide a method of relieving the discomfort of breast engorgement pain and the drying of breast milk without the administration drugs.

It is an additional object of the present invention to provide a device of the type stated which is highly efficient, and easy to use.

It is another object of the present invention to provide other benefits to be determined through consumer testing and/or clinical trial, including but not limited to treatment of prolactin dependent and related diseases.

Consequently, this invention resides in the novel features form, construction, arrangement and combination of part presently described and pointed out in the claims.

An appreciation of the other aims and objectives of the present invention and an understanding of it may be achieved by referring to the accompanying drawings and description of a preferred embodiment.

BRIEF DESCRIPTION OF THE DRAWINGS

Figure 1:
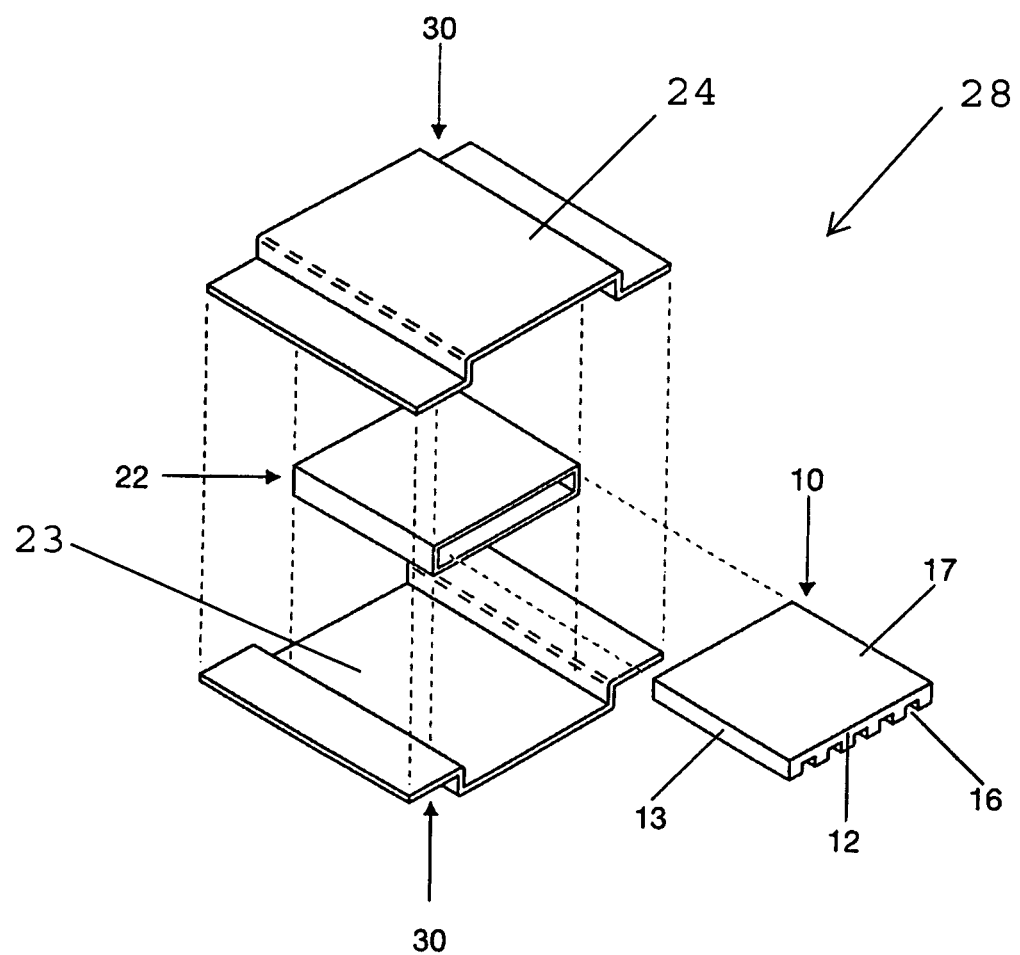

Having thus described the invention in general terms, reference will now be made to the accompanying drawings in which:

FIG. 1 is an exploded, perspective view of the Holistic Breast Patch 28: the Telfa® pad 30 which is gauze lined on the interior side 23 and non-adherent perforated film bonded on the exterior side 24; gauze 22; the "Carbonyl Group" disc 10 and the Telfa® pad 30 embodying the present invention.

Figure 2:
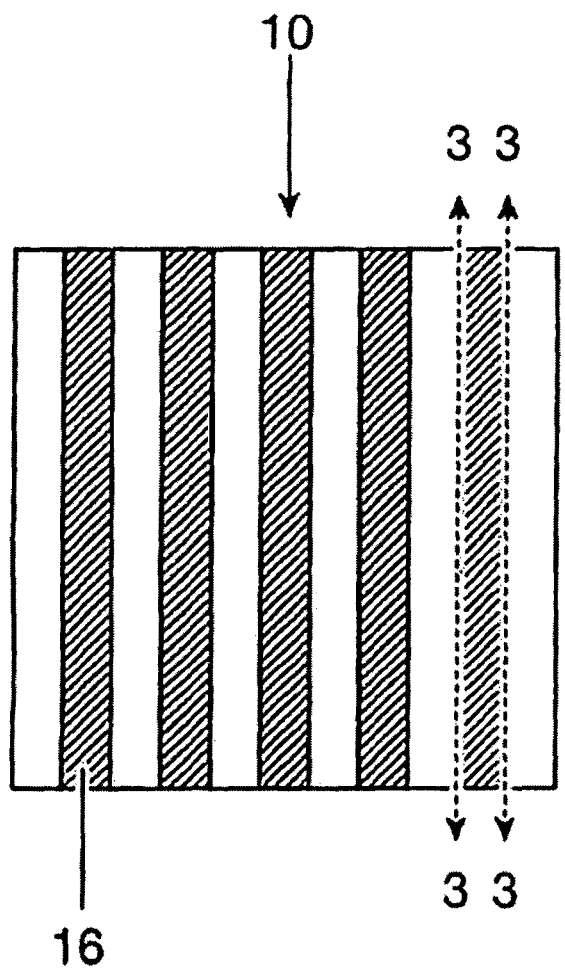

FIG. 2 is a bottom plan view of the disc 10 illustrating the grooves 16.

Figure 3:
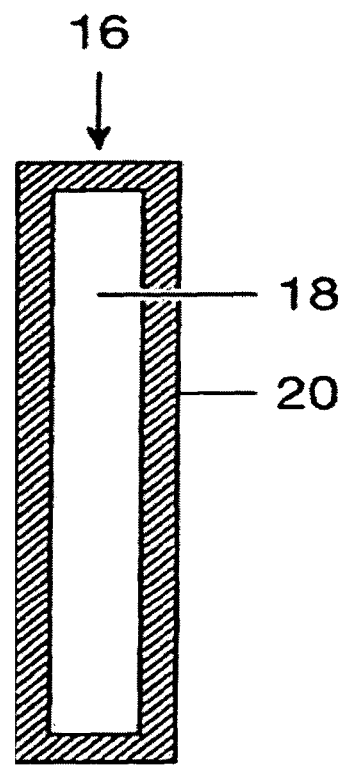

FIG. 3 is a vertical sectional view of the grooves 16 also designating the inner and outer core 18 and 20 through the interior of the "Carbonyl Group" disc 10 taken along line 3-3 of FIG. 2.

Figure 4:
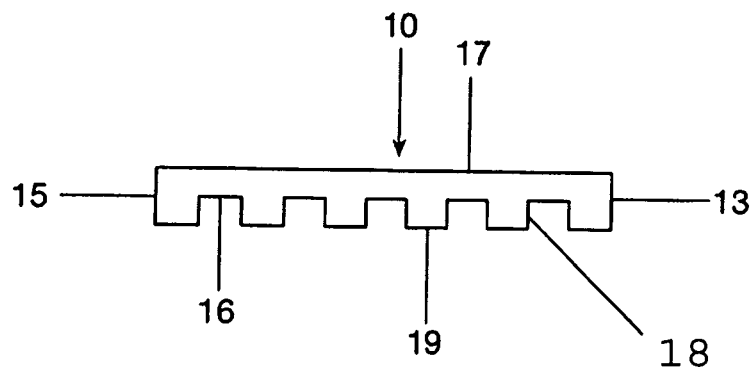

FIG. 4 is an elevational view of the disc 10 facing side 12 or 14 with the top facing up.

Figure 5:
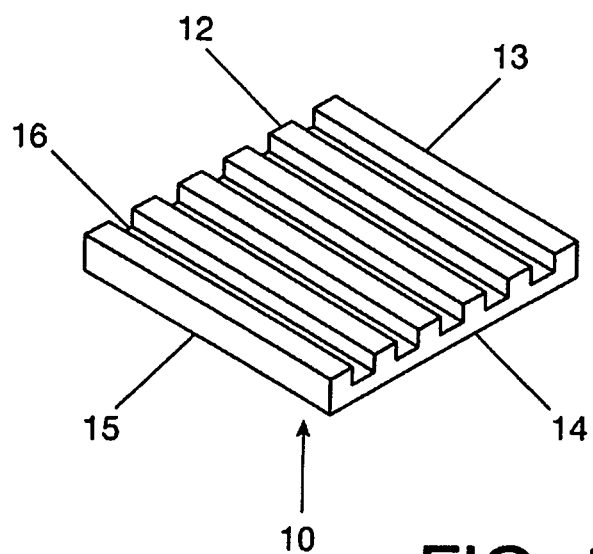

FIG. 5 is a perspective view of the disc 10 with the bottom facing up.

DETAILED DESCRIPTION OF THE PREFERRED EMBODIMENT

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

Explaining now the process of making and using this unique invention, reference characters to the drawings which illustrate a preferred embodiment of the invention will also be made in order to give a description in more detail.

The designated lactation suppression and engorgement pain relief device, the Holistic Breast Patch, is worn by postpartum women, generally in the form of a sterile Telfa® pad consisting of inactive ingredients: a thin film 24 of polyethylene terephthalate lined with a thin layer of cotton gauze 23. As shown in FIG. 1, this Telfa® pad 30 is the exterior housing for the disc 10 which houses the active ingredients: ("Formula" R—Co—R) nickel, manganese, phosphorus, silicon, sulfur, and carbon) in the form of an interior disc. This formula is called "Carbonyl Group".

FIG. 1 is an exploded, perspective view of the Holistic Breast Patch 28. It comprises a first Telfa® pad 30; gauze 22; the "Carbonyl Group" disc 10; and a second Telfa® pad 30. Telfa® pads are gauze lined on the interior side 23 and have non-adherent perforated film bonded on the exterior side 24.

As shown in the Figures, the preferred embodiment is constructed initially as a thin flexible, flat disc 10. This Carbonyl Group disc 10 is about 0.75 inch square, has a top flat surface 17, a bottom grooved surface, and is provided with four very thin sides 12, 13, 14 and 15.

The inner core of the disc 10 is preferably constructed by forming a piece of high carbon content metal into the shape of a flat disc and this forming may be by stamping the same from a sheet of such metal.

The inner core 18 should preferably have a thickness of about 49.7 mils, although this can range from about 49.7 mils to about 49.9 mils. The essentially pure nickel outer layer 20 should have a thickness of about 0.3 mils, although the thickness of the outer layer 20 may range from about 0.1 mils to about 1.0 mil.

The entire disc 10 is preferred to have an overall thickness of about 50 mils, that is, from the top 17 to the bottom 19. This thickness is preferred since the disc 10 will then have the necessary structural integrity, although it will not be unduly heavy. However, it should be understood that the thickness of the disc 10 could vary, depending upon the desired thickness of the inner core 18 and of the outer layer 20, as hereinafter described.

The metal which is employed as the inner core 18 contains a substantially high carbon content, as aforesaid. This carbon content could be 0.7% by weight to about 1.5% by weight. In a more preferable range, the amount of carbon would range from about 0.6% to about 0.9% referred to as high carbon steel. The remaining content of the inner core would be formed of basic metal elements which would include some minor amounts of manganese, chromium, and possibly a minor amount of nickel. The minor amounts of these other components, such as manganese, chromium, and possibly even nickel, would be less than about 1.0%.

Extending between the sides 12 and 14, and parallel to the sides 13 and 15 of the disc 10, are a plurality of elongated grooves 16 or openings. These grooves 16 constitute openings on the rear face 19 of the disc 10. They serve as air holes and also as relief for the disc 10 to bend to conform to the different chest curvatures of the user but do not extend in depth through the front surface 17 of the disc 10. The grooves 16 are depressed to a depth of about 25 mils, although they could be depressed into the disc 10 for a depth of about 40 mils.

The distance between each of the grooves 16 is preferably about 0.075 inches (75 mils) and the width of each groove 16 is about 0.075 inches (75 mils). In connection with the invention, it is preferred that the width of the grooves 16 is equal to the width of the space between each of the grooves 16.

By reference to the drawings, it can be seen that the interior disc 10 is comprised of an inner core 18 of a metal containing a high carbon content and which is enclosed within an outer nickel layer 20. The outer nickel layer is substantially pure nickel.

In a slightly different embodiment of the invention, the metal elements used in the formation of the disc 10 would include the carbon and the nickel in the percentages as aforesaid. However, minor amounts of other elements would also be in the composition and these include, for example, phosphorus in an amount of 0.6% by weight, and silicon in an amount of 0.30% by weight. Manganese may be present in an amount of about 0.60% by weight. Vanadium, molybdenum and chromium may also be present in minor trace amounts. The phosphorus could actually range from about 0.4% to about 1.0%. The manganese could also range from about 0.1% to about 0.8%, and the silicon could also range from about 0.1% to about 0.8%.

The aforesaid composition provides a disc 10 of substantial hardness. However, it is not unduly brittle, and moreover, it is still flexible providing curvature and has a moderately light weight so that it can be worn comfortably and easily by a user The invention can further be embodied such that the grooves 16 constitute openings which extend between sides 12 and 14, 25 to 40 mils in length. FIG. 1, FIG. 4 and FIG. 5 illustrate an embodiment in which the grooves are located on one flat surface 19 of the disc 10, but do not extend all the way through from flat surface 17 to flat surface 19.

The interior disc 10 of the Patch which is all natural and organic is adapted to be seated between cotton gauze on both sides and then two Telfa® pads 30 as shown in FIG. 1.

The exterior housing of the disc consists of Telfa® inner lined with cotton gauze, FIG. 1. Telfa® is FDA approved under the classification of various bandages and consists of a thin layer of absorbent cotton fibers, enclosed in a sleeve of polyethylene terephthalate, and bonded with a thin layer of a perforated non-adherent film. This film does not adhere to the skin therefore, eliminating discomfort when removed. The Telfa® and cotton are inactive ingredients.

This milk suppression aid device was constructed by forming a piece of high-carbon content metal into the shape illustrated in FIG. 1 and FIG. 2. The disc has the overall dimension of 0.75 inch square, FIG. 2. The width of the spaces between each of the grooves 16 is 0.075 inches and the width (horizontal dimension) of each of the individual grooves 16 themselves is 0.075 inches.

The overall device 10 has a thickness of 343 mils or approximately ⅓ inch. The grooves 16 have a depth into the device 10 of about 20 mils on each of the flat faces. The thickness of the inner core 18 of high-carbon metal is about 49.7 mils and the thickness of the outer layer 20 of nickel is about 0.3 mils.

Notably, the success of this invention resides in the wearing of the Patch between the woman's breasts. For optimal results women who will not be breast-feeding should start wearing the breast patch within twenty-four hours after child delivery. It should be worn continuously until engorgement pain and milk production cease. However, positive results are still achieved when started more than twenty-four hours after delivery.

One of the important aspects of this disc is that it does cause any adverse effects. The use of the disc for the purpose of aiding the drying of breast milk and relieving breast engorgement pain has been explored in conjunction with interaction with commonly used drugs. The interaction, if any, is set forth below:

| DRUG | INTERACTION |
|---|---|
| Ampicillin | None known |
| Anticoagulants | None known |
| Anticonvulsant hydantoin | None known |
| Antidepressants tricyclic (TEA) | None known |
| Anti-diabetic agents | None known |
| Antihistamines | None known |
| Barbiturates | None known |
| Chloramphenicol | None known |
| Clofibrate | None known |
| Dextrothyroxine | None known |
| Guanethidine | None known |
| Hypoglycemic (oral) | None known |
| Insulin | None known |
| Meperidine | None known |
| Meprobamate | None known |
| Mineral oil | None known |
| Non-steroidal anti-inflammatory drugs (NSAID's) | None known |
| Rifampin | None known |
| Sulfadiazine and Pyrimethamine | None known |
| Terazosin | None known |
| Tetracyclic | None known |
| Urosodiol | None known |
| Vitamin A | None known |
| Vitamin E | None known |
| Anticoagulants (oral) | None known |
| Anti-diabetic (oral) | None known |
| Carbamazepine | None known |
| Phenobarbital | None known |
| Primidone | None known |
| Tamoxifen | None known |
| Thyriodhormones | None known |
| Bromocriptine | None known |
| 33, Hypoglycemic (oral) | None known |
| Oxyphenbutazone | None known |
| Phenothiazines | None known |
| Phenylbutazone | None known |

The use of the Holistic Breast Patch has also been explored for possible interaction with other substances. The interaction with several substances, or lack thereof, is set forth below.

| SUBSTANCE | COMBINED EFFECT |
|---|---|
| Alcoholic beverages | None Known |
| Nonalcoholic beverages | None Known |
| Cocaine | None Known |
| Foods/salt | None Known |
| Marijuana | None Known |
| Tobacco/all forms | None Known |

EXAMPLES

The invention is further illustrated, but not limited to, the following examples:

Example 1

The Holistic Breast Patch aid device was used by a group of ten women. Each of the women was provided the device within twenty-four hours after giving birth. After wearing the device between the breasts for three to five days each of the women reported that lactation was suppressed.

Example 2

The aid device was again used by a group of ten women. Each of the women was provided the device almost immediately after delivery. In each case, the birth was a normal delivery. After wearing the device between the breasts for three to five days, engorgement of the breasts was reduced.

Thus, there has been illustrated and described a unique and novel device and method for aiding suppression of milk after pregnancy and relieving breast engorgement pain which, therefore, fulfills all of the objects and advantages which have been sought. It should be understood that many changes, modifications, variations and other uses and applications will become apparent to those skilled in the art after considering this specification and the accompanying drawings.

Therefore, any and all such changes, modifications, variations and other uses and applications which do not depart from the spirit and scope of the invention are deemed to be covered by the invention. The claims of said device are inclusive of but not limited to the descriptions and claims in the Specification. Having thus described our invention, what we desire to claim and secure by Application for Letters Patent are the following.

What is claimed is:

1. A holistic breast patch comprising:
    a) a disc of high carbon steel surrounded by nickel, wherein the disc has a front surface and a rear surface; said rear surface being grooved;
    b) a gauze sleeve, having a first side and a second side, surrounding said disc; said first side being adjacent said front surface and said second side being adjacent said rear surface;
    c) a first film of polyethylene terephthalate connected to said first side of said gauze sleeve;
    e) a second film of polyethylene terephthalate connected to said second side of said gauze sleeve; and
    f) said first and second film extend beyond said gauze sleeve and connect to one another.

* * * * *